United States Patent [19]

Nicolau et al.

[11] Patent Number: 4,473,563

[45] Date of Patent: * Sep. 25, 1984

[54] LIPID VESICLES CONTAINING INOSITOL HEXAPHOSPHATE

[75] Inventors: Yves-Claude Nicolau, Mulheim; Klaus Gersonde, Aachen, both of Fed. Rep. of Germany

[73] Assignee: Studiengesellschaft Kohle MBH, Mulheim, Fed. Rep. of Germany

[*] Notice: The portion of the term of this patent subsequent to Mar. 11, 1997 has been disclaimed.

[21] Appl. No.: 317,676

[22] Filed: Nov. 2, 1981

Related U.S. Application Data

[60] Division of Ser. No. 23,044, Mar. 22, 1979, Pat. No. 4,321,259, which is a continuation-in-part of Ser. No. 909,081, May 24, 1978, abandoned, which is a continuation-in-part of Ser. No. 832,867, Sep. 13, 1977, abandoned.

[30] Foreign Application Priority Data

Sep. 6, 1977 [DE] Fed. Rep. of Germany ....... 2740053

[51] Int. Cl.$^3$ ............................................. A61K 31/66
[52] U.S. Cl. .................................. 424/224; 424/199; 424/343; 424/365; 424/101
[58] Field of Search ............... 424/199, 101, 343, 224, 424/365

[56] References Cited

U.S. PATENT DOCUMENTS 4,192,869  3/1980  Nicolau et al. .................... 424/199

Primary Examiner—Sam Rosen
Attorney, Agent, or Firm—Sprung, Horn, Kramer & Woods

[57] ABSTRACT

The invention provides erythrocytes of improved $O_2$-release properties having fused thereto small allosteric effectors, f.i. inositol hexaphosphate-containing lipid vesicles. Also included in the invention is a method for making said erythrocytes and plasma containing said erythrocytes. This application is specifically directed to said inositol hexaphosphate-containing lipid vesicles.

8 Claims, 22 Drawing Figures

LIPID VESICLES CONTAINING INOSITOL HEXAPHOSPHATE

This application is a divisional application of Ser. No. 23,044 filed Mar. 22, 1979, now U.S. Pat. No. 4,321,259, which in turn is a continuation-in-part application of application Ser. No. 909,081, filed May 24, 1978, now abandoned, which in turn is a continuation-in-part application of application Ser. No. 832,867, filed Sept. 13, 1977, now abandoned.

One of the major functions of erythrocytes consists in the transport of molecular oxygen from the lungs to the peripheral tissues. The erythrocytes contain a high concentration of haemoglobin (Hb) (30 pg per cell=35.5 g/100 ml cells) which forms a reversible adduct with $O_2$. The $O_2$-partial pressure in the lung is ~100 mm Hg, in the capillary system ~70 mm Hg against which $O_2$ must be dissociated from the oxygenated haemoglobin. Under physiological conditions only about 25% of the oxygenated haemoglobin may be deoxygenated; ~75% is carried back to the lungs with the venous blood. Thus, the major fraction of the Hb—$O_2$ adduct is not used for the $O_2$ transport.

Interactions of Hb with allosteric efforts enable an adaptation to the physiological requirement of maximum $O_2$ release from the Hb—$O_2$ adduct with simultaneous conservation of the highest possible $O_2$-partial pressure in the capillary system.

Hb's allosteric properties are responsible for the sigmoid shape of the $O_2$-binding curve. Its half-saturation pressure ($p_{O_2}(\frac{1}{2})$) is an indicator of the $O_2$ affinity. The slope of the sigmoid curve in the range of 40 to 60% saturation represents the degree of cooperativity of the four $O_2$-binding sites in Hb (Hill coefficient: n=2.8–3.2). An increase of the Hill coefficient, i.e. a steeper slope of the sigmoid binding curve, or a shift of the entire binding curve towards higher $O_2$-partial pressure (so-called "right-shift") would lead to a facilitated $O_2$ release in the capillary system and to an improved oxygen supply to the surrounding tissues. A "right-shift" is actually achieved in vivo by the enhancement of the 2,3-bisphosphoglycerate level in erythrocytes and its binding to haemoglobin. Binding of 2,3-bisphosphoglycerate to Hb decreases the $O_2$ affinity and increases the $O_2$ half-saturation pressure. 2,3-bisphosphoglycerate synthesized in the glycolysis bypass in erythrocytes is an effector for slow adaptation to $O_2$ deficiency.

2,3-bisphosphoglycerate increases the half-saturation pressure of stripped haemoglobin at pH 7.4 from $p_{O_2}(\frac{1}{2})=9.3$ mm Hg (37° C.), and 4.3 mm Hg (25° C.) to $p_{O_2}(\frac{1}{2})=23.7$ mm Hg (37° C.), and 12.0 mm Hg (25° C.), respectively (Imai, K. and Yonetani, T. (1975), J. Biol. Chem. 250, 1093–1098). A significantly stronger decrease of the $O_2$ affinity, i.e. enhancement of the $O_2$ half-saturation pressure has been achieved for stripped haemoglobin by binding of inositol hexaphosphate (phytic acid; IHP) (Ruckpaul, K. et al. (1971) Biochim. Biophys. Acta 236, 211–221) isolated from vegetal tissues. Binding of IHP to haemoglobin increases the $O_2$ half-saturation pressure to $p_{O_2}(\frac{1}{2})=96.4$ mm Hg (37° C.), and $p_{O_2}(\frac{1}{2})=48.4$ mm Hg (25° C.), respectively. IHP, like 2,3-bisphosphoglycerate and other polyphosphates cannot permeate the erythrocyte membrane.

Lipid vesicles reflect some of the properties of cell membranes. They can penetrate into cells either by fusion with the cell plasma membrane or by endocytosis (Papahadjopoulos, D. et al. (1976) Nature 252, 163–165). The fusion plays an important part in a number of membrane processes like: Synaptic transmission, secretion, plasma membrane assembly, infection with enveloped viruses. The fusion of cells with lipid vesicles was achieved in cell cultures and with erythrocyte ghosts.

Treatment of ML cells (cell line-murine lymphoma) with vesicles containing IgG with a high neutralizing titer against Coxsackie virus A-2 L protected the cells against subsequent infection with this virus. Gregoriadis and Buckland (Nature (1973) 235, 252–253) have used lipid vesicles in order to incorporate invertase into invertase-defective mouse macrophages. In vivo experiments though, did not lead to unambiguous results since the lipid vesicles are incorporated indiscriminately by all cells or are quickly destroyed in the liver.

The use of lipid vesicles for the incorporation of allosteric effectors or of other substances into erythrocytes has not been reported so far. Many experiments have shown that lipid vesicles can be injected into animals without danger.

Whereas the influence of IHP on the structure and function of isolated Hb has been studied in detail there are no data about the interaction of IHP with haemoglobin in intact erythrocytes, as it was not possible, until now, to incorporate IHP into intact erythrocytes.

SUMMARY OF THE INVENTION

Surprisingly, we found that using fluid-charged lipid vesicles, which can fuse with the erythrocyte membrane, it was possible to transport allosteric effectors as IHP into erythrocytes where, due to its much higher binding constant it replaces 2,3-bisphosphoglycerate at its binding site in haemoglobin. Under these conditions Hb in erythrocytes changes into an allosteric conformation with a significantly lower $O_2$ affinity.

The lowering of the $O_2$ affinity, i.e. the enhancement of the $O_2$ half-saturation pressure of haemoglobin in erythrocytes, increases the capacity of erythrocytes to dissociate the bound $O_2$ even against higher $O_2$-partial pressures and thus improves the $O_2$ supply to the tissues.

Erythrocytes, having incorporated IHP and which therefore provide an improved $O_2$ supply to the tissues may find their use in the following cases:

1. Under low $O_2$-partial pressure in the inhaled air: Mountain climbers at high altitudes, astronautes in $O_2$-poor atmosphere.
2. In the case of reduced $O_2$-exchange surface: Decrease of the number of pulmonary alveoles in lung emphysema.
3. Increased resistance to $O_2$ diffusion in the lung: Pneumonia, Asthma.
4. Decreased $O_2$-transport capacity: Erythropeny, anaemic states of all types, arteriovenous shunt.
5. Blood circulation disturbances: Arteriosclerosis, thromboembolic processes, organ infarct, ischaemic states.
6. High $O_2$ affinity of haemoglobin: Haemoglobin mutations, chemical modifications of N-terminal amino acids in the haemoglobin-chains e.g. Diabetes mellitus, enzyme defects in erythrocytes.
7. Acceleration of detoxication processes by improved oxygen supply.
8. In order to decrease the $O_2$-affinity of conserved blood: Transfusion, shock states.
9. Improvement of radiotherapy of cancer.

As allosteric effectors for the incorporation into erythrocytes are used which have a larger affinity to haemoglobin than the known physiologic effectors, 2,3-bisphosphoglycerate and adenosine triphosphate.

Specifically inositol hexaphosphate is preferred as allosteric effector.

Other sugar phosphates as inositol pentaphosphate, inositol tetraphosphate, inositol triphosphate, inositol diphosphate and diphosphatidyl inositol diphosphate can be used as allosteric effectors.

Further allosteric effectors are other polyphosphates as nucleotide triphosphates, nucleotide diphosphates, nucleotide monophosphates, and alcohol phosphate esters are suitable.

In case of certain mutations of haemoglobin, f.i. "Züurich" haemoglobin, organic anions as polycarboxylic acids can be used as allosteric effectors.

Finally, it is possible to use inorganic anions as as hexacyano ferrate, phosphate or chloride as allosteric effectors.

Lipid vesicles are mixtures of phosphatidylchloine/-phosphatidylserine/cholesterol which are used in a mole ratio of 10 to 5:4 to 1:10 to 3. In place of the phosphatidylserine, one can substitute an equivalent molar amount of stearoylamine, phosphatidic acid, phosphatidyl inositolphosphate or lysophosphatidyl choline. Specifically favored is a mole ratio of 8:2:7, but also a mole ratio of 9:1:8 as well as 8:4:7 is favorable.

As fluid carrier the customary liquid carrier, specifically buffered physiologic carriers are used which are known, f.i. isotonic bis-Tris buffer.

The lipid vesicles must be able to fuse with the membrane of the erythrocytes. By the incorporation of allosteric effectors into intact erythrocytes it is possible now that haemoglobin of the erythrocytes is transferred into an allosteric conformation which releases oxygen easier.

By the invention it is possible to produce modified erythrocytes which guarantee an improved oxygen economy of the blood. These modified erythrocytes are obtained by irreversible incorporation of allosteric effectors which takes place by fusing lipid vesicles into the erythrocyte membranes and binding the allosteric effectors so introduced into the erythrocytes to the haemoglobin.

If for example IHP is used as allosteric effector, first, lipid vesicles are loaded with IHP and then fused with erythrocytes after which IHP is bound to the haemoglobin whereby the allosteric conformation of the haemoglobin and therewith its affinity to oxygen is changed.

The incorporation of the combination of allosteric effectors and lipid vesicles into the erythrocytes is conducted extracorporal.

During the application and use erythrocytes are separated from drawn blood, modified by the incorporation of lipid vesicles together with allosteric effectors and the modified erythrocytes refed to the blood plasma. Therefore, it is possible to preserve stored blood containing modified erythrocytes.

The modified erythrocytes can be used also included in a physiologic carrier for injection or transfusion into a blood circle.

A specific manner to prefer modified erythrocytes according to the invention can be described as follows:

(a) Inositol hexaphosphate is dissolved in an isotonic buffer until the solution is saturated, (b) the mixture of lipid vesicles is suspended in the solution of (a), the mole ratio of phosphatidylcholine, phosphatidylserine and cholesterol being in the range of 10 to 5:4 to 1:10 to 3, (c) the sole prepared suspension is disintegrated by ultrasonic treatment or by an injection process, (d) the mixture is centrifuged and the upper suspension separated. This upper suspension contains the inositol hexaphosphate rich, small lipid vesicles as well as free inositol hexaphosphate, (e) human erythrocytes separated from blood plasma by centrifuging are suspended in the upper suspension of (d), (f) during incubation the vesicles fuse into the erythrocytes, (g) the now modified intact erythrocytes are washed with isotonic NaCl solution or isotonic buffer, whereby free inositol hexaphosphate are quantitatively removed. Thereafter the prepared erythrocytes are suspended in blood plasma or blood substitute.

BRIEF DESCRIPTION OF THE DRAWINGS

Following is a brief description of the drawings:

FIG. 18: A plot of IHP concentration of inside-outside medium [M] versus $O_2$ half-saturation pressure, $P_{O_2(\frac{1}{2})}$ [mm Hg].

FIG. 19: A plot of added volume of 0.19 M IHP [m] versus $O_2$ half-saturation pressure, $P_{O_2(\frac{1}{2})}$ [mm Hg].

FIG. 20: A plot of added volume of V2 vesicle suspension [ml] versus $O_2$ half-saturation pressure, $P_{O_2(\frac{1}{2})}$ [mm Hg].

FIG. 21: A plot of relative right-shift of $P_{O_2(\frac{1}{2})}$ [%] versus relative altitude adaption [%].

FIG. 22: A plot of $P_{O_2}$[mm Hg] versus $O_2$ saturation [%].

DETAILED DESCRIPTION OF THE INVENTION

The degree of oxygen desaturation of intra-erythrocytic haemoglobin in the capillaries depends not only on the venous $O_2$-partial pressure but above all on the oxygen affinity of the haemoglobin in the red cells. Intra-erythrocytic allosteric effectors controlling the $O_2$ affinity are Bohr protons, $CO_2$ and organic phosphate compounds particularly DPG (2,3-bisphosphoglycerate-natural allosteric effector) and ATP (adenosine triphosphate).

Figure 1:
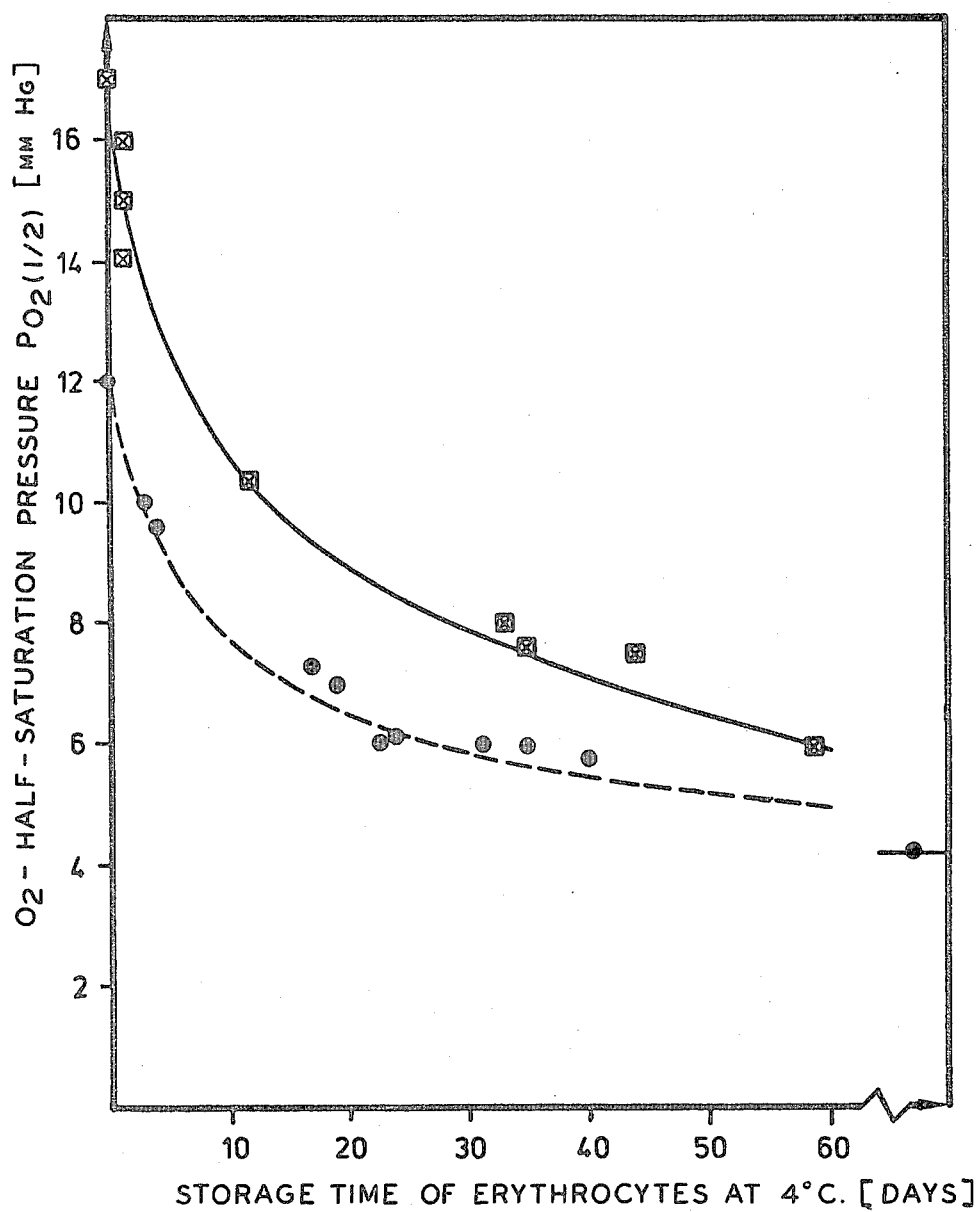
FIG. 1: Increase of $O_2$ affinity of intra-erythrocytic haemoglobin with storage time at 4° C. The $O_2$ half-saturation pressure, $p_{O_2}(\frac{1}{2})$ was measured at 25° C. in the absence of $CO_2$. Red blood cells (RBC) stored in ACD, $\psi$ and in isotonic 0.10 M bis-Tris buffer pH 7.4 containing 0.154 molar NaCl -●- —-●-respectively.

The depletion of DPG and ATP in stored red cells leads to a progressive increase of the oxygen affinity (Balcerzak, S. et al. (1972) Adv. Exp. Med. Biol. 28, 433–447) demonstrated in FIG. 1 by plotting the $O_2$-partial pressure at half-saturation (measured at 25° C.) versus the storage time (erythrocytes stored at 4° C.). The $O_2$-binding isotherms are measured in the absence of $CO_2$ and at constant pH (pH 7.4) in order to preclude influences of these allosteric effectors on the half-saturation pressure. The end point of the progressive polyphosphate depletion is defined by $p_{O_2}(\frac{1}{2})=4.2$ mm Hg, which is the half-saturation pressure of totally phosphate-free (stripped) haemoglobin; the starting point, i.e. $p_{O_2}(\frac{1}{2})$ of fresh erythrocytes, depends on the composition of the suspending medium. From these polyphosphate depletion curves a new functional parameter of stored erythrocytes can be determined, the so-called half-life time of intra-erythrocytic polyphosphate. It is 9 d (days) in isotonic 0.1 M bis-Tris buffer pH 7.4 and 12 d (days) in ACD (acid-citrate-dextrose: conservation solution) stabilisator solution.

The depletion of polyphosphates in erythrocytes causes a "left-shift" of the $O_2$-binding isotherm and therefore a decrease of the capacity of oxygen release.

Figure 2:
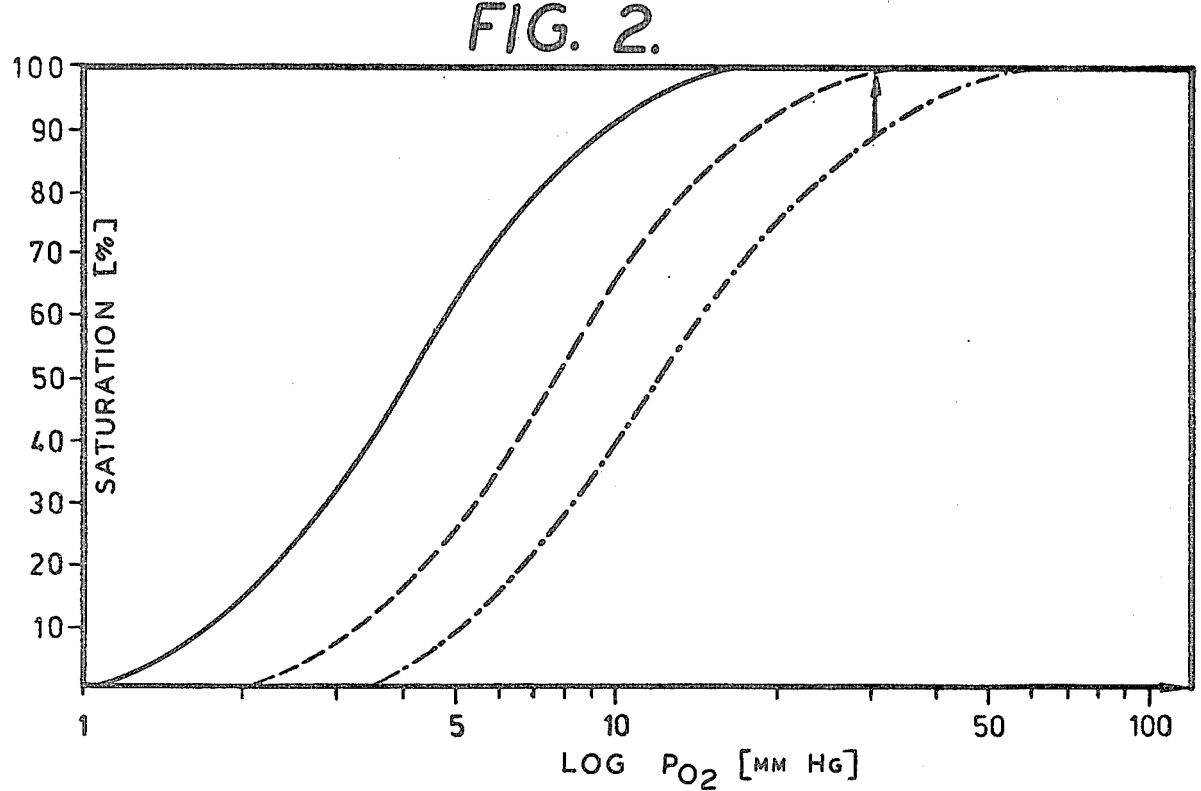
FIG. 2: "Left-shift" of the $O_2$-binding curves of intra-erythrocytic haemoglobin depending on the storage time at 4° C. RBC stored in isotonic 0.10 M bis-Tris buffer pH 7.4 containing 0.154 molar NaCl at 4° C. Binding isotherms were measured at 25° C. in the absence of $CO_2$._____: RBC totally depleted of polyphosphates;-------: RBC at half-life time of polyphosphate depletion ($\tau_{\frac{1}{2}}$=9 d); -.-.-.-.-.: fresh RBC. Arrow indicates desaturation of haemoglobin under the $O_2$-partial pressure of 30 mm Hg.

The "left-shift" of the $O_2$-binding curve and the decrease of the capacity of oxygen release of at 4° C. stored erythrocytes at 25° C. are shown in FIG. 2. Under an $O_2$-partial pressure of 30 mm Hg the desaturation of fresh erythrocytes reaches 11%, whereas erythrocytes being half-depleted of polyphosphates desaturate only to 1%.

Figure 3:
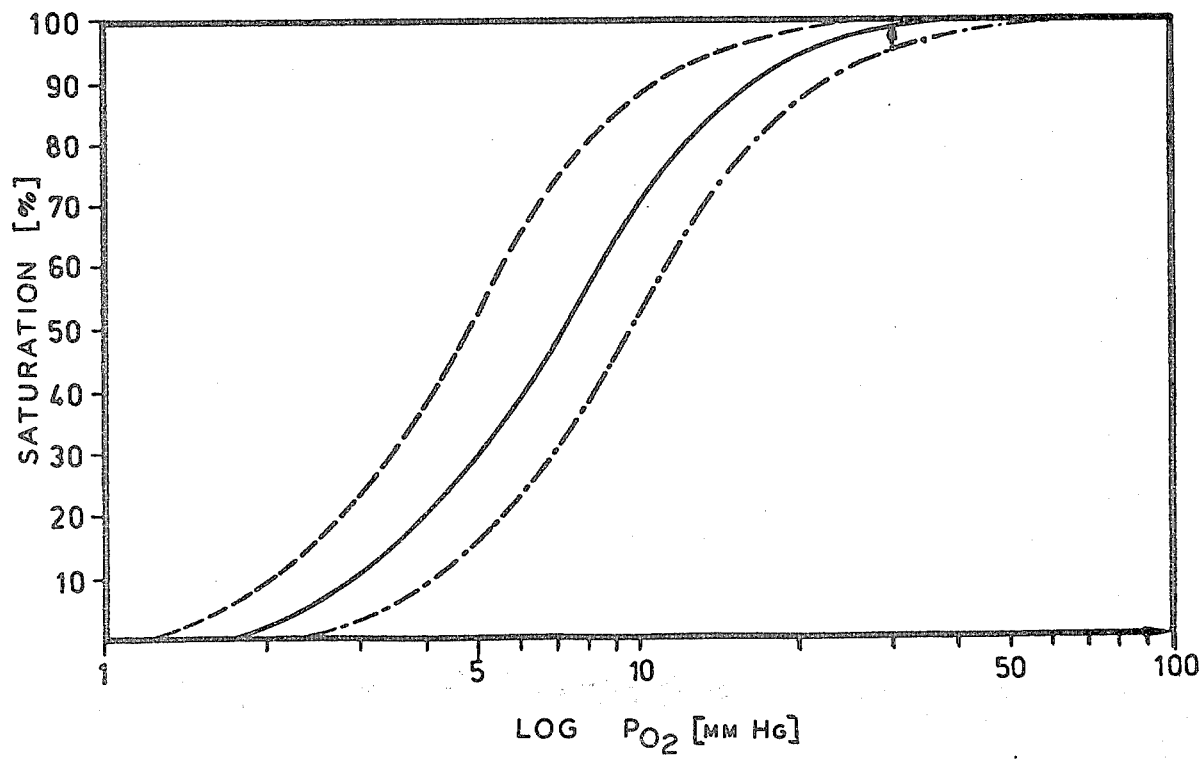
FIG. 3: pH dependence of $O_2$-binding curves at 25° C. in the absence of $CO_2$. RBC stored 17 days at 4° C. in isotonic 0.10 M bis-Tris buffer pH 7.4 containing 0.154 molar NaCl: ---------, pH 7.72; ———: pH 7.42; -.-.-.-.-.: pH 7.08. Arrow indicates desaturation of haemoglobin under the $O_2$-partial pressure of 30 mm Hg.
Figure 4:
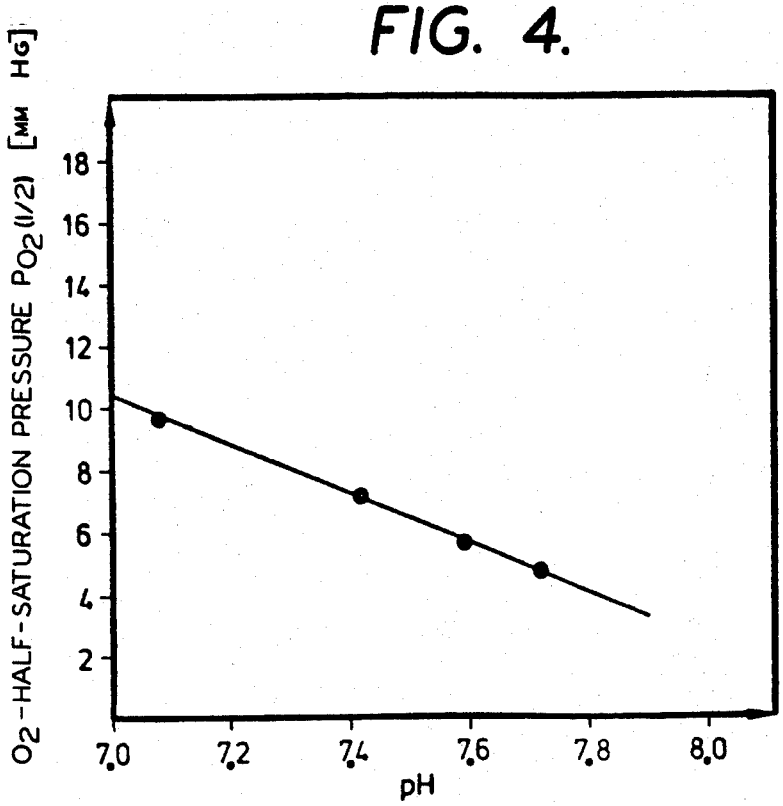
FIG. 4: Bohr effect of intra-erythrocytic haemoglobin at 25° C. in the absence of $CO_2$. RBC stored 17 days at 4° C. in isotonic 0.10 molar bis-Tris buffer pH 7.4 containing 0.154 molar NaCl.

The "left-shift" of the $O_2$-binding curves of polyphosphate-depleted erythrocytes causes impairing of oxygen delivery in the tissues. Thus a massive transfusion of stored blood (being DPG deficient) results in a fall in muscle pH and an increase of the lactate level in the plasma accompanied by a fall of the blood pressure known as the "Transfusion-Syndrome" (Kevy, S. V. et al. (1972) Adv. Exp. Med. Biol. 28, 511–516). This decrease in pH only partially counter-regulates the "left-shift" demonstrated in FIG. 3. For an $O_2$-partial pressure of 30 mm Hg shift of the pH from 7.42 to 7.08 increases the oxygen desaturation of red cells (stored for 17 d at 4° C. in isotonic 0.1 M bis-Tris buffer pH 7.4) from 1% to 5%; but a desaturation of 11% observed with fresh red cells at pH 7.46 cannot be effected by the Bohr effect alone (see FIG. 2). The influence of pH on the $O_2$ affinity (Bohr effect) of stored red cells suspended in isotonic 0.1 M bis-Tris and Tris buffers, respectively, is shown in FIG. 4 for the range of pH 7.0 to 7.8. The $O_2$-binding curves are measured at 25° C. and in the absence of $CO_2$ with erythrocytes stored for 17 days at 4° C. These aged erythrocytes have lost more than half of their polyphosphate effect on the $O_2$ affinity of haemoglobin (see FIG. 1). The Bohr effect, $-\Delta p_{O_2}(\frac{1}{2})/\Delta pH$, amounts to 0.53 protons per mole $O_2$. The number of Bohr protons released with oxygen binding is constant at least up to an RBC age of 34 days when already 75% of the polyphosphate effect is lost. Therefore storage, i.e. depletion of polyphosphates, has no effect on the Bohr effect of the erythrocytes.

METHODS

Collection and storage of human blood:

A volume of 100 ml blood was drawn from a young healthy volunteer and collected into a 250 ml-Bioflask (Biotest-Serum-Institut, Frankfurt a. Main) containing 50 ml ACD stabilisator. This sample was stored at 4° C.

Collection and storage of human erythrocytes:

A volume of 300 ml blood drawn from a young proband was collected into a plastic bag which contained heparin or sodium citrate for preventing blood clotting. The blood sample was chilled in an ice bath and further work was carried out at 4° C. Erythrocytes were separated from the plasma by centrifugation at 23500 xg for 20 minutes (Sorvall, Type RC-2B; Rotor SS 34; 12000 rpm). The packed red cells were suspended in isotonic pH 7.4 saline bis-Tris buffer (0.10 molar bis-Tris, 0.154 molar NaCl) and centrifuged; this washing procedure was repeated three times. Finally, the packed erythrocytes were suspended in 300 ml isotonic saline bis-Tris buffer pH 7.4 and stored at 4° C.

pH measurement and adjustment of the erythrocyte suspension:

The red cells stored in isotonic 0.1 M buffers pH 7.4 and ACD respectively were centrifuged at room temperature for 2 minutes at 8000 xg (Eppendorf Centrifuge, Type 3200; 12000 rpm). The desired pH of the erythrocyte suspension was adjusted by repeated exchange of buffering medium. The cells were suspended in the desired buffer and again centrifuged; this procedure has to be repeated until a constant pH is reached.

The pH is measured at 25° C. with a glass electrode (Ingold, Frankfurt a. Main, Typ. 406-M3, a=35 mm). The accuracy of the pH measurement is ±0.02 units.

Preparation of the IHP-loaded lipid vesicles:

IHP was dissolved for instance between room temperature and 50° C. in an isotonic bis-Tris buffer (0.10 molar bis-Tris, 0.154 molar NaCl) pH=7.4 up to saturation (0.19 M). A lipid mixture consisting of phosphatidylcholine (PC): phosphatidylserine (PS):cholesterol (Ch) in the molar ratios 8:2:7 (see Table 1) was suspended in this solution and sonicated 45 min under nitrogen at ~50° C. The temperature range for vesicle preparation is limited only by the freezing point of the buffer and by the thermal stability of the polyphosphate. The sonication was performed with a ultrasonic disintegrator (Schöller, Type 125, Frankfurt a. Main) with a titan dip-probe (10 kHz). Sonication can be effectively performed at energies preferably above 100 W/cm². After sonication the vesicle suspension was centrifuged for 1 h at 100000 xg at 25° C. in an ultracentrifuge (Beckmann, Typ L5-65, Rotor 60). The supernatant contains the small lipid vesicles, with a diameter of ≦500 Å. When the vesicles are formed they include the solution in which the lipds are suspended.

TABLE 1

| Composition of the lipid vesicles[+] | |
|---|---|
| Vesicles | PC:PS:Ch molar ratios |
| V1 | 9:1:8 |
| V2 | 8:2:7 |
| V3 | 8:4:7 |
| V4 | 8:0:7 |

[+]Operable molar ratio ranges (V1–V3) = PC:PS:Ch = 10–5 . 4–1:10–3.

Phosphatidylserine was from bovine brain (Koch-Light, GB) and phosphatidylcholine from egg yolk (Lipid Specialties, Boston, USA). Cholesterol and the sodium salt of inositol hexaphosphate were purchased from Merck (Darmstadt) and Sigma (München) respectively. All lipids were purified by column chromatography and their purity was checked by thin layer chromatography. 1 nmol/1 of lipid yields $2 \times 10^{11}$ lipid bilayer vesicles (small vesicles, d≦500 Å). $2 \times 10^{11}$ lipid vesicles were incubated with $10^6$ erythrocytes, but other ratios were used as well, as it will be seen below.

Incorporation of inositol hexaphosphate into human erythrocytes.

For in vitro experiments a volume of 200 μl erythrocyte suspension was centrifuged at room temperature for 2 min at 8000 xg (Eppendorf Centrifuge, Type 3200, 12000 rpm). If necessary, the packed cells were washed and adjusted to the desired pH as described above and then resuspended in a volume of 200 μl isotonic 0.1 M buffer of desired pH. To this an equal volume of the lipid vesicle suspension of desired pH was added. The erythrocytes were incubated for 1 h at 37° C. The erythrocytes were then repeatedly washed with isotonic 0.1 M buffer until a constant pH value was reached. Precipitation tests with $Ca^{2+}$ were carried out with the supernatant until no free IHP could be detected anymore. Any buffer system effective in pH range 7 to 8 which does not affect the structural, morphological and functional integrity of the erythrocytes may be used.

Measurement of the $O_2$-binding curves:

$O_2$-binding curves were measured at 25° C. by means of the rapid diffusion technique (Sick, H. and Gersonde, K. (1969), Analyt. Biochem. 32, 362–376; Sick, H. and Gersonde, K. (1972), 47, 46–56).

RESULTS

Bohr effect of stored human red cells after fusion with vesicles.

$O_2$ half-saturation pressure, cooperatively (n=2.8) and Bohr effect of human erythrocytes stored for 40 days in isotonic buffering medium pH 7.4 at 4° C. and partially depleted of polyphosphates are not significantly changed after incubation in isotonic pH 7.6 buffer with vesicles V2 at 37° C. for 1 h. Furthermore, incubation of erythrocytes with vesicles having different lipid compositions (V1 and V3) has also no effect on the $O_2$-binding parameters of the intra-erythrocytic haemoglobin.

Bohr effect of stored human red cells after vesicle-mediated (V2) incorporation of inositol hexaphosphate.

IHP, the strongest allosteric effector of haemoglobin known up to now decreases the $O_2$ affinity of haemoglobin indicated by a "right-shift" of the $O_2$-binding curve. Human erythrocytes not being able to synthesize IHP can be loaded with this polyphosphate during fusion with lipid vesicles containing the effector. The experiments described by this invention exemplified by IHP incorporation would essentially go in the same direction with all kinds of allosteric effectors, f.i. sugar phosphates as inositol pentaphosphate, inositol tetraphosphate, inositol triphosphate, inositol diphosphate, and diphosphatidyl inositol diphosphate, further polyphosphates as nucleotide tri-, di-, and monophosphates, alcohol phosphate esters. Inorganic anions (hexacyanoferrat(II), phosphate and chloride) with effector properties, as well as mixtures thereof, which are unable to cross the erythrocyte membrane can be used. Also in specific cases of haemoglobin which show a mutation, organic anions as polycarboxylic acids can be used as allosteric effectors. As example for the polycarboxylic acid maleic acid can be used in cases of "Zürich" haemoglobin.

Figure 5:
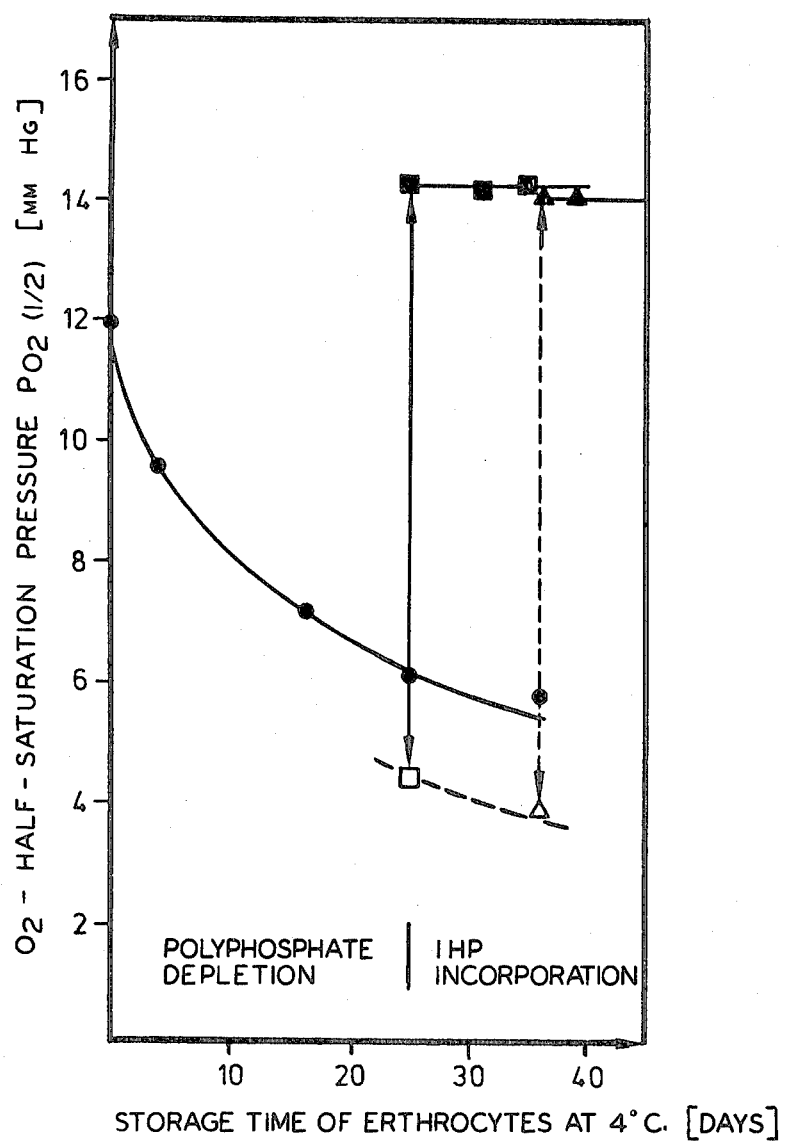
FIG. 5: Irreversible IHP incorporation into red cells; $O_2$ half-saturation pressure of erythrocytes measured at 25° C. and in the absence of $CO_2$ before and after V2-mediated IHP incorporation at pH 7.6. RBC stored at 4° C. in isotonic 0.10 bis-Tris buffer pH 7.4 containing 0.154 molar NaCl; -●-●-●- : polyphosphate depletion curve of RBC; □←—→■ : IHP incorporation at pH 7.6 and storage of IHP-loaded RBC at 4° C.; △←—→▲ : IHP incorporation at pH 7.6 and storage of IHP-loaded RBC at 37° C. IHP incorporation carried out under standard conditions.

Human erythrocytes stored at 4° C. in isotonic buffering medium pH 7.4 for 25 days ($p_{O_2}(\frac{1}{2})=6.0$ mm Hg) were adjusted to pH 7.6 ($p_{O_2}(\frac{1}{2})=4.5$ mm Hg) and then incubated for 1 h at 37° C. in isotonic pH 7.6 0.1 molar Tris buffer containing 0.19 molar IHP with IHP-loaded V2 vesicles. After IHP incorporation into erythrocytes the $O_2$ half-saturation pressure increases drastically ($p_{O_2}(\frac{1}{2})=14.3$ mm Hg) by a factor of 3.2 and exceeds the value for fresh erythrocytes. ($p_{O_2}(\frac{1}{2})=10.55$ mm Hg) by a factor of 1.4. Then these IHP-loaded erythrocytes were stored at 4° C. in isotonic pH 7.6 buffering medium for 6 days; the half-saturation pressure remained constant. After further 4 days storage at 4° C. the IHP-loaded erythrocytes were changed to pH 7.28 and the $p_{O_2}(\frac{1}{2})$ increased again to 32.1 mm Hg. In other experiments, washed erythrocytes stored at 4° C. for 36 days (more depleted of DPG) were adjusted to pH 7.6 and IHP incorporated as described above. Again the $p_{O_2}(\frac{1}{2})$ increased to 14.0 mm Hg. The IHP-loaded cells were stored at 37° C. for 2 days. No change in $O_2$ affinity was observed either after storing these IHP-loaded cells at 37° C. for 2 days. Contrary to normal erythrocytes which show during storage at 4° C. half-depletion of physiological polyphosphates, IHP-loaded erythrocytes do not seem to hydrolyse IHP during at least 9 days indicated by a constant $p_{O_2}(\frac{1}{2})$ value (see FIG. 5). Thus, substantially longer storage times can be achieved with the so treated erythrocytes.

Figure 6:
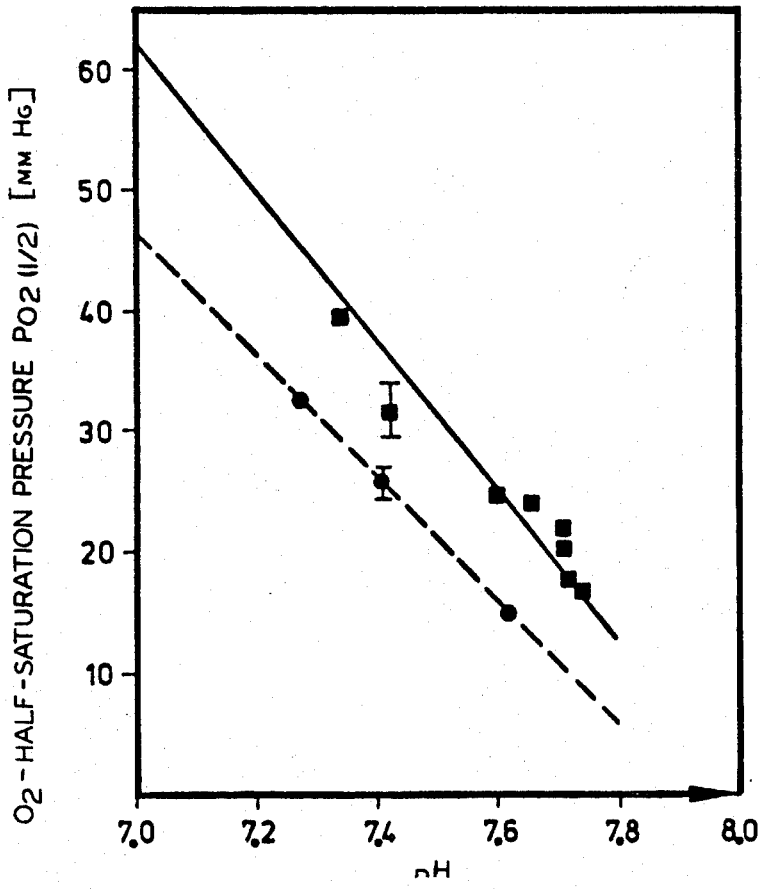
FIG. 6: Bohr effect of IHP-loaded erythrocytes at 25° C. in the absence of $CO_2$. -●-●-●- : V2-mediated IHP incorporation at pH 7.6; -■-■-■- : V2-mediated IHP incorporation at pH 7.8. RBC stored at 4° C. in isotonic 0.10 molar bis-Tris buffer pH 7.4 containing 0.154 molar NaCl; IHP incorporation carried out under standard conditions.

In addition to the IHP-loaded red cells are showing a Bohr effect larger than of the non-treated cells (see FIG. 6).

In the absence of $CO_2$ the Bohr effect of erythrocytes incubated with IHP-loaded V2 vesicles in the presence of free IHP at pH 7.6 and adjusted to the desired pH by washing with the respective isotonic 0.1 M buffer amounts to $-\Delta p_{O_2}(\frac{1}{2})/\Delta pH = 1.20$ protons per mole $O_2$. The Bohr proton release of IHP-loaded erythrocytes is 3 times larger than in normal fresh red cells. Therefore IHP-loaded cells make the oxygen release in the tissues and the oxygen uptake in the lungs more efficient. Incorporation of IHP with IHP-loaded V2 vesicles in the presence of free IHP is much more efficient at pH 7.8. After having changed the pH of the IHP-loaded cells to 7.4 the theoretically expected increase to $p_{O_2}(\frac{1}{2})=35$ mm Hg can be observed (see FIG. 6). On the other hand the Bohr effect seems to become smaller ($-\Delta p_{O_2}(\frac{1}{2})/\Delta pH=0.9$ protons per mole $O_2$) after incorporation at pH 7.8.

Effect of vesicle composition on the inositol hexaphosphate uptake by human erythrocytes.

The amount of IHP taken up by human erythrocytes is measured as the extent of "right-shift" of the $O_2$-binding curve. Thus the $O_2$ half-saturation pressure measured under standard conditions is an expression of the efficiency of incorporation. This efficiency of the IHP uptake depends largely on the lipid composition of the vesicles.

Figure 7:
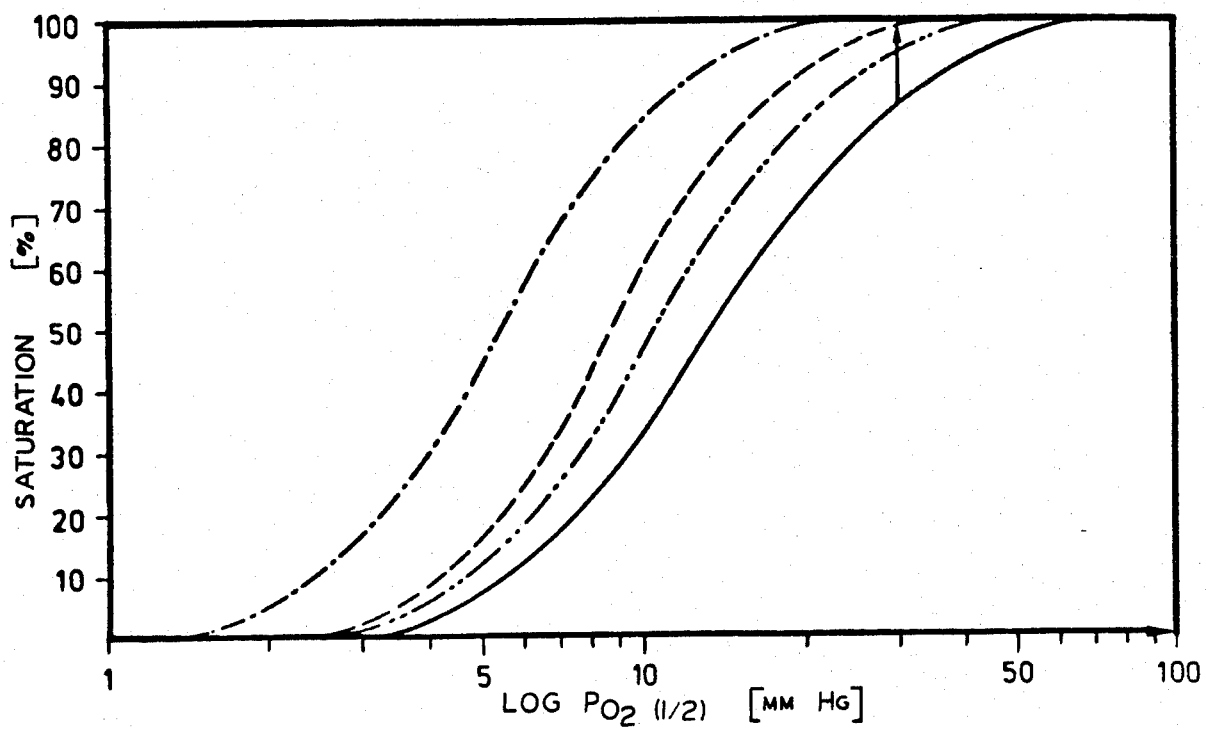
FIG. 7: Influence of vesicle composition on the "right-shift" of $O_2$-binding isotherms measured for pH 7.6 at 25° C. in the absence of $CO_2$. IHP incorporation at pH 7.6 was carried out under standard conditions and cells were suspended in isotonic buffer pH 7.6. -.-.-.-.-.- : RBC 19 days stored in isotonic 0.10 molar bis-Tris buffer pH 7.4 containing 0.154 molar NaCl; ---------- : RBC after V1-mediated IHP incorporation; ——·——· ——— : fresh RBC; _____ : RBC after V2-mediated IHP incorporation. Arrow indicates desaturation of haemoglobin under the $O_2$-partial pressure of 30 mm Hg.

In FIG. 7 the "right-shift" of the $O_2$-binding curve is demonstrated for the V1 and V2 vesicles after incubation at pH 7.6 V2 vesicles show the largest "right-shift" with a desaturation of 14% at 30 mm Hg. Erythrocytes, 19 days old, show no desaturation at this $O_2$ pressure, fresh red cells, however, desaturate to 5%. The incorporation of IHP with V2 vesicles improves the $O_2$ delivery of the normal red cells at 30 mm Hg by a factor of about 3. V2 and V3 vesicles induce identical IHP uptake by erythrocytes and therefore identical "right-shifts" of the $O_2$-binding curves.

In the absence of IHP in the outer medium V1, V2 and V3 vesicles, having included IHP, do not differ with regard to their half-life time of incorporation, $\tau_{\frac{1}{2}}$, being 30 min. V1 and V3 show only less than the half of the IHP effect measured for dialyzed IHP-loaded V2 vesicles.

Figure 8:
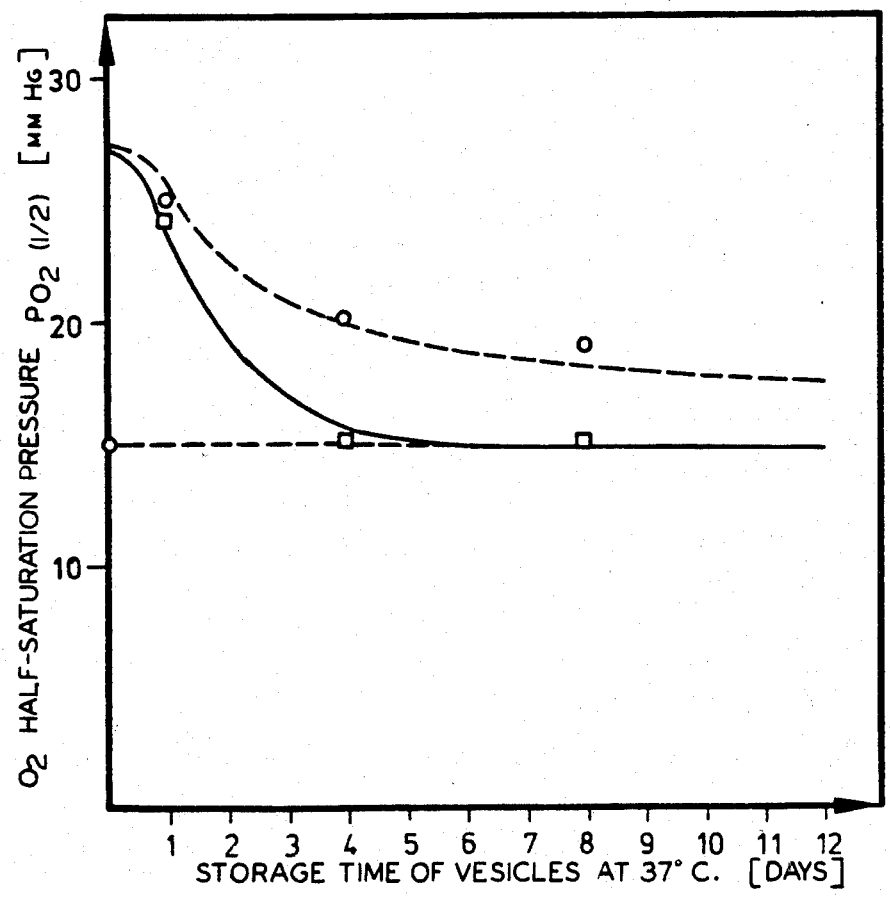
FIG. 8: Stability of IHP-loaded vesicles at 37° C. -⊖- -⊖-⊖- V2 vesicle; -⊟-⊟-⊟- : V3 vesicle. Vesicle-mediated IHP uptake by RBC at pH 7.4 under standard conditions. $p_{O_2}(\frac{1}{2})$ of IHP-loaded erythrocytes measured at 25° C. in the absence of $CO_2$.

This indicates a reduced stability of V1 and V3. In FIG. 8 the difference in stability of V2 and V3 is demonstrated. V2 has a half-life time of stability of about 3 days, V3 of about 1.5 days.

Figure 9:
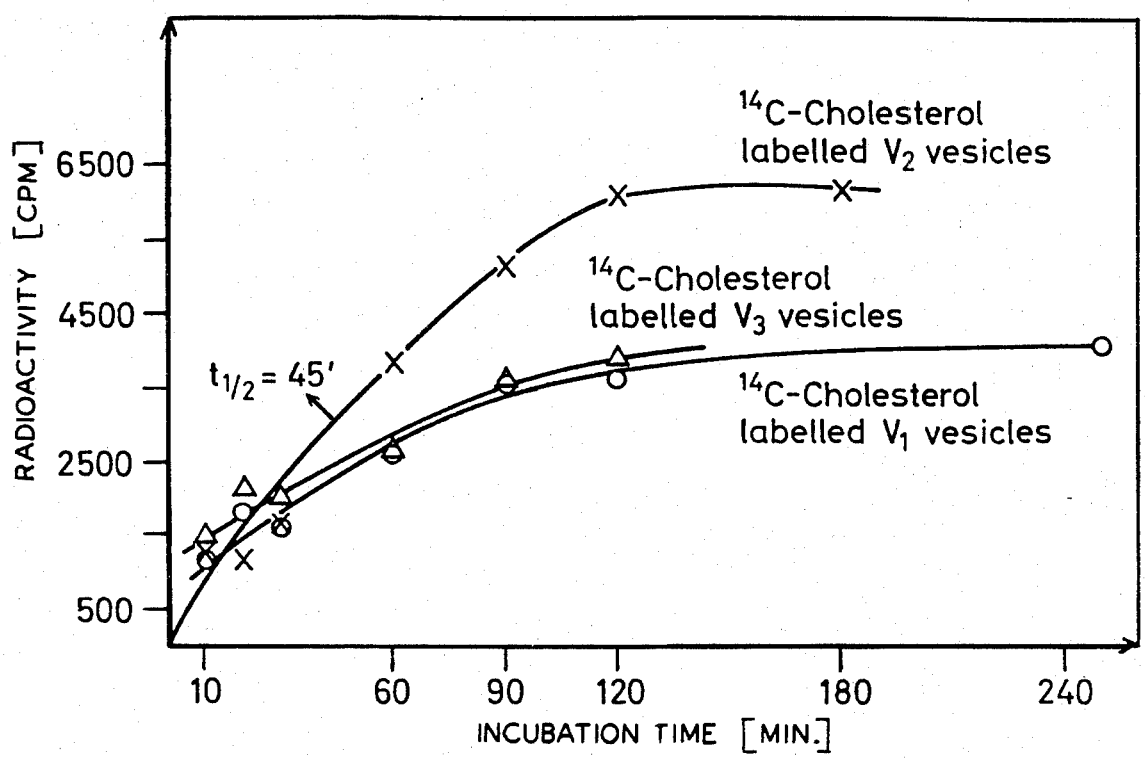
FIG. 9: Kinetics of incorporation of $^{14}C$-cholesterol from vesicles into intact erythrocytes. Incubation was carried out at 37° C. in isotonic 0.1 molar bis-Tris buffer pH 7.4 containing 0.154 molar NaCl.
Figure 10:
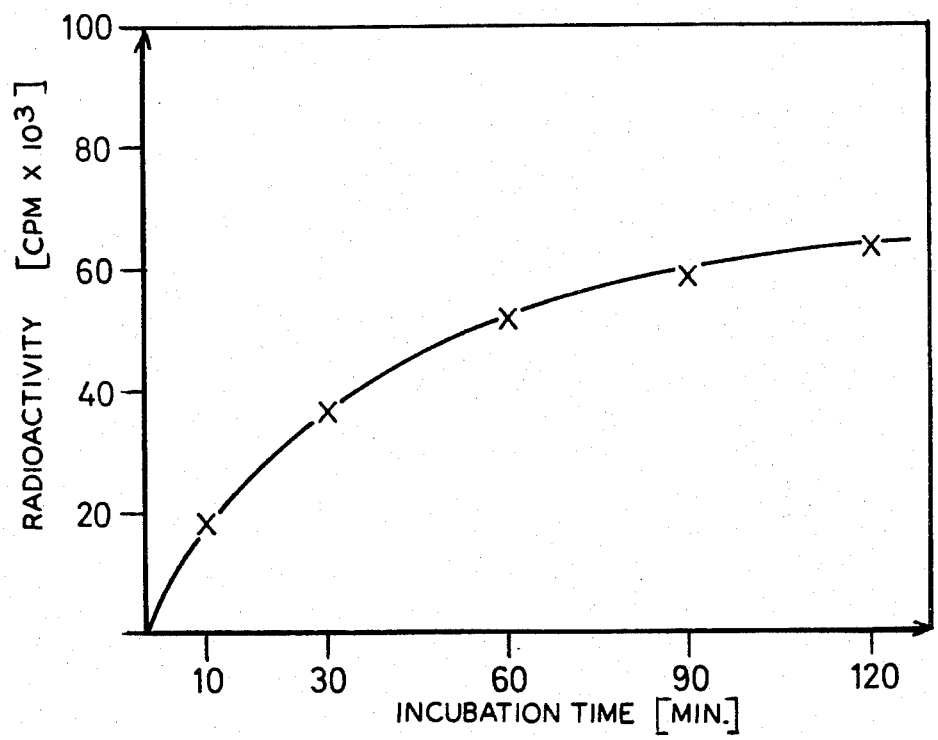
FIG. 10: Kinetics of incorporation of $^{14}C$-cholesterol from V2-vesicles into intact erythrocytes. Radioactivity measured in Folch extracted lipids of the erythrocytes. Conditions of incubation as in FIG. 9.
Figure 11:
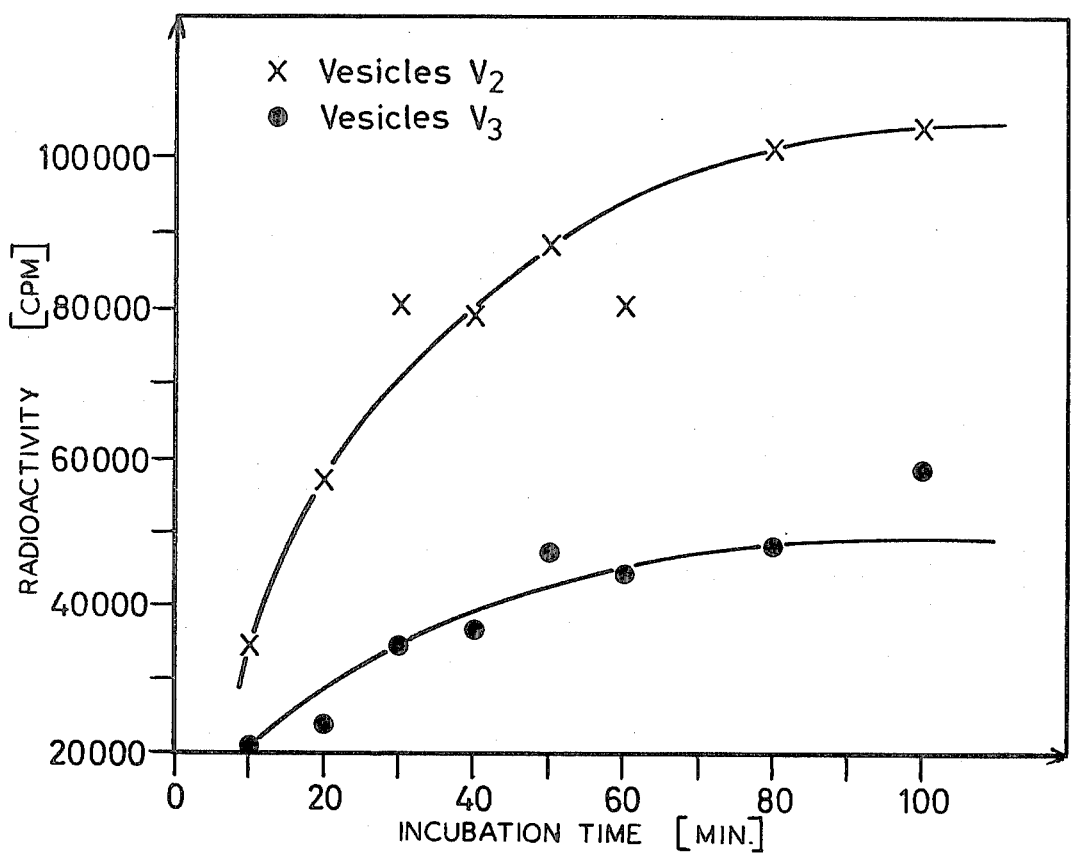
FIG. 11: Kinetics of $_{14}C$-cholesterol uptake by Hela cells from lipid vesicles. Incubation at 37° C. in phosphate buffered saline pH=7.4.
Figure 12:
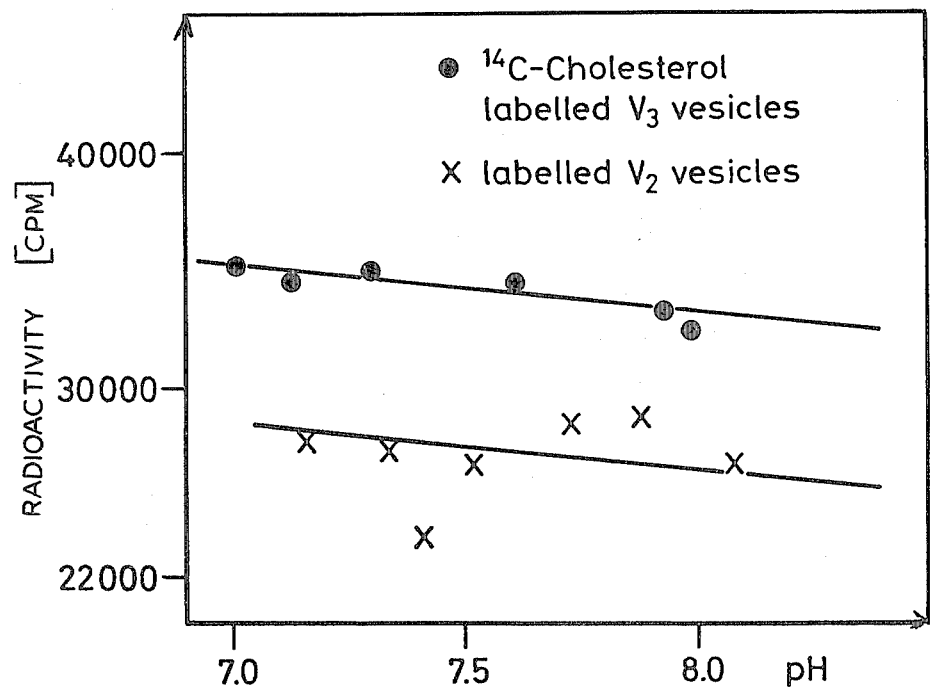
FIG. 12: pH dependence of $^{14}C$-cholesterol uptake by Hela cells from vesicles. Conditions as in FIG. 11.

Incorporation of the vesicles into cells:

The incorporation of the lipid vesicles into intact erythrocytes was followed with the vesicles V1, V2, V3 labelled with $^{14}C$-cholesterol or $^{14}C$-phosphatidylcholine. This was compared with the incorporation of the same vesicles in cultured Hela cells. The radioactivity was assayed both in the intact erythrocytes (by solubilization and bleaching with a Lumac reagents kit) and in their total lipid Folch extracts. The incorporation was followed over a period of 4 hours. The results are shown in FIGS. 9 and 10. FIG. 9 shows the data for the vesicles V1, V2 and V3 with intact erythrocytes. The incubation medium contained 10 ml RBC (red blood cells), 10 ml IHP-loaded vesicles in isotonic 0.1 M bis-Tris buffer pH 7.4. Aliquots were taken after 10, 20, 40, 60, 90, 120, 180, 240 minutes and counted. The half-life time of incorporation is 45 min for the V2 vesicles (which show also the highest radioactivity level in the RBC) and 35 min for V1 and V3. It has to be stressed that the radioactivity found in the RBC does not necessarily indicate vesicle incorporation, as it is well known (Bloj, B. and Zilversmit, D. (1977) Biochemistry 16, 3943–3948) that cholesterol exchanges between vesicles and erythrocytes. In the RBC lipid extracts (see FIG. 10) we find a $\tau_{\frac{1}{2}}$ of 30 min when V2 vesicles were used. When V2 and V3 vesicles are incorporated into Hela cells the same pattern is obtained (see FIG. 11). The incubation of the Hela cells with the vesicles was made under the same conditions as described before. In another set of experiments, Hela cells were incubated with $^{14}C$-cholesterol-containing vesicles in isotonic buffers, at several pH values between 7 and 8. FIG. 12 shows that the pH variations between 7–8 had little influence on the incorporation of the labelled lipid by the cells.

Figure 16:
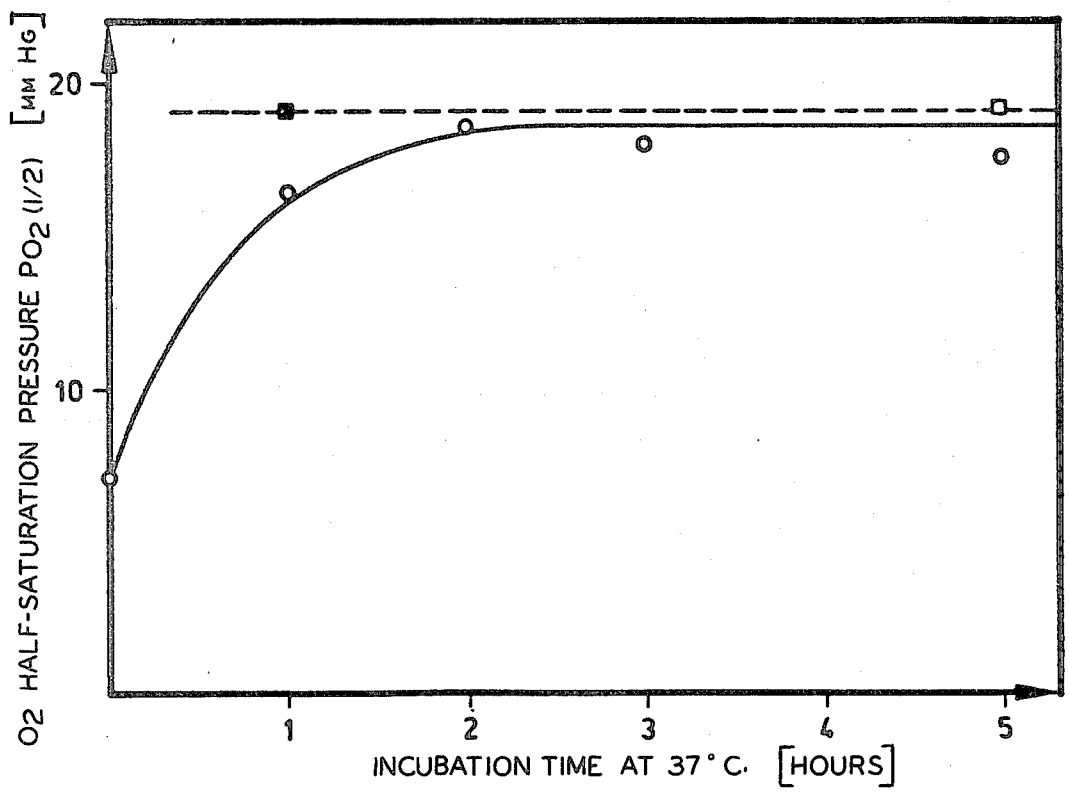
FIG. 16: Kinetics of the V2-mediated IHP incorporation by erythrocytes at pH 7.4 in the absence of IHP in the outer medium. Incubation was carried out under standard conditions. $p_{O_2}(\frac{1}{2})$ was measured at 25° C. in the absence of $CO_2$.

The half-life time of the radioactivity uptake by the erythrocytes, when incubated with radioactively labelled vesicles is the same as the half-life time of the IHP uptake by erythrocytes incubated with dialyzed, IHP-loaded vesicles (FIG. 16). This is additional proof that we measure not only lipid exchange between cells and vesicles but fusion of vesicles with the cells.

Thin layer chromatograms of the erythrocyte lipid extract showed the enrichment of the RBC membrane lipids with the lipids of the vesicles.

Apparent pH-optimum of the V2-mediated IHP uptake by stored human red cells.

The uptake of IHP by washed erythrocytes depends on the pH of the incubation medium. Plotting $p_{O_2}(\frac{1}{2})$ of IHP-loaded erythrocytes versus pH of incubation medium (see FIG. 13) demonstrates an apparent pH optimum of IHP incorporation in the range of pH 7.4 to 7.5. The decrease of $p_{O_2}(\frac{1}{2})$ above pH 7.5 corresponds to the Bohr effect curve shown in FIG. 6 and correlates with the decrease of IHP affinity to haemoglobin. Below pH 7.4 the dramatic decrease of $p_{O_2}(\frac{1}{2})$ indicates a limited IHP incorporation and therefore the theoretically expected $p_{O_2}(\frac{1}{2})$ for totally transformed haemoglobin by bound IHP is not observed.

The change of buffering medium to pH 7.4 after incubation at pH 7.8 increases the $p_{O_2}(\frac{1}{2})$ of intra-erythrocytic haemoglobin to values of 30 to 40 mm Hg at 25° C. as demonstrated in FIG. 6. Incubation at pH 7.8 and buffering to different pH-values lead to an increase of $p_{O_2}(\frac{1}{2})$ over the whole range of pH. From this result we can conclude that incorporation of IHP into erythrocytes is more effective above pH 7.4 although at lower pH values are also effective.

Kinetics of the IHP uptake by stored human red cells.

Figure 13:
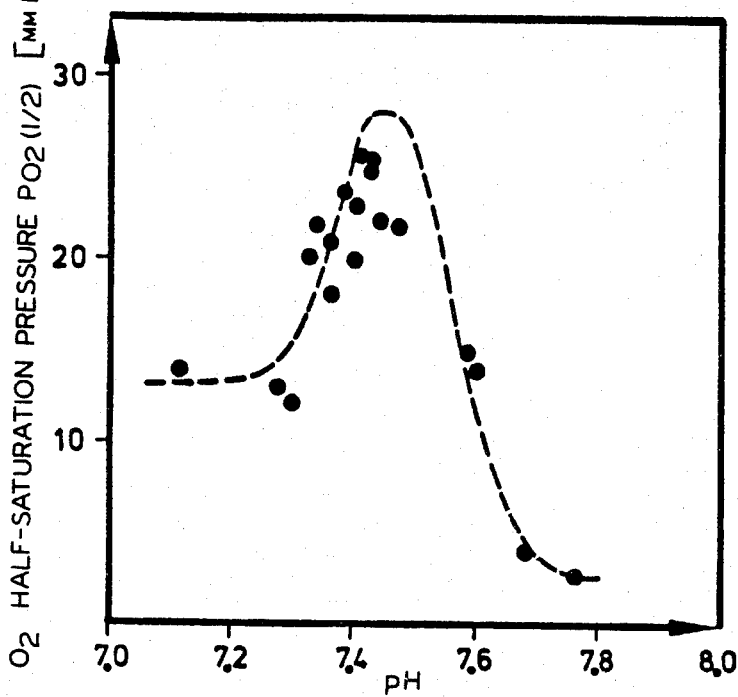
FIG. 13: Influence of pH of incubation medium on the $O_2$-half-saturation pressure of IHP-loaded erythrocates. $p_{O_2}(\frac{1}{2})$ measured at 25° C. in the absence of $CO_2$.
Figure 15:
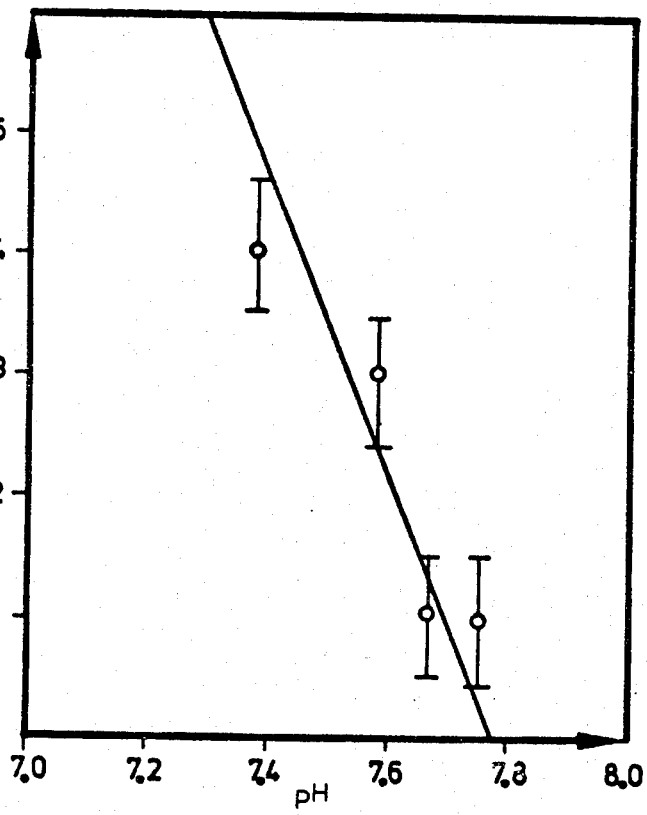
FIG. 15: Influence of pH of incubation medium on the half-life time of V2-mediated IHP incorporation. RBC was incubated under standard conditions with IHP in the outer medium. $p_{O_2}(\frac{1}{2})$ measured at 25° C. in the absence of $CO_2$.
Figure 14:
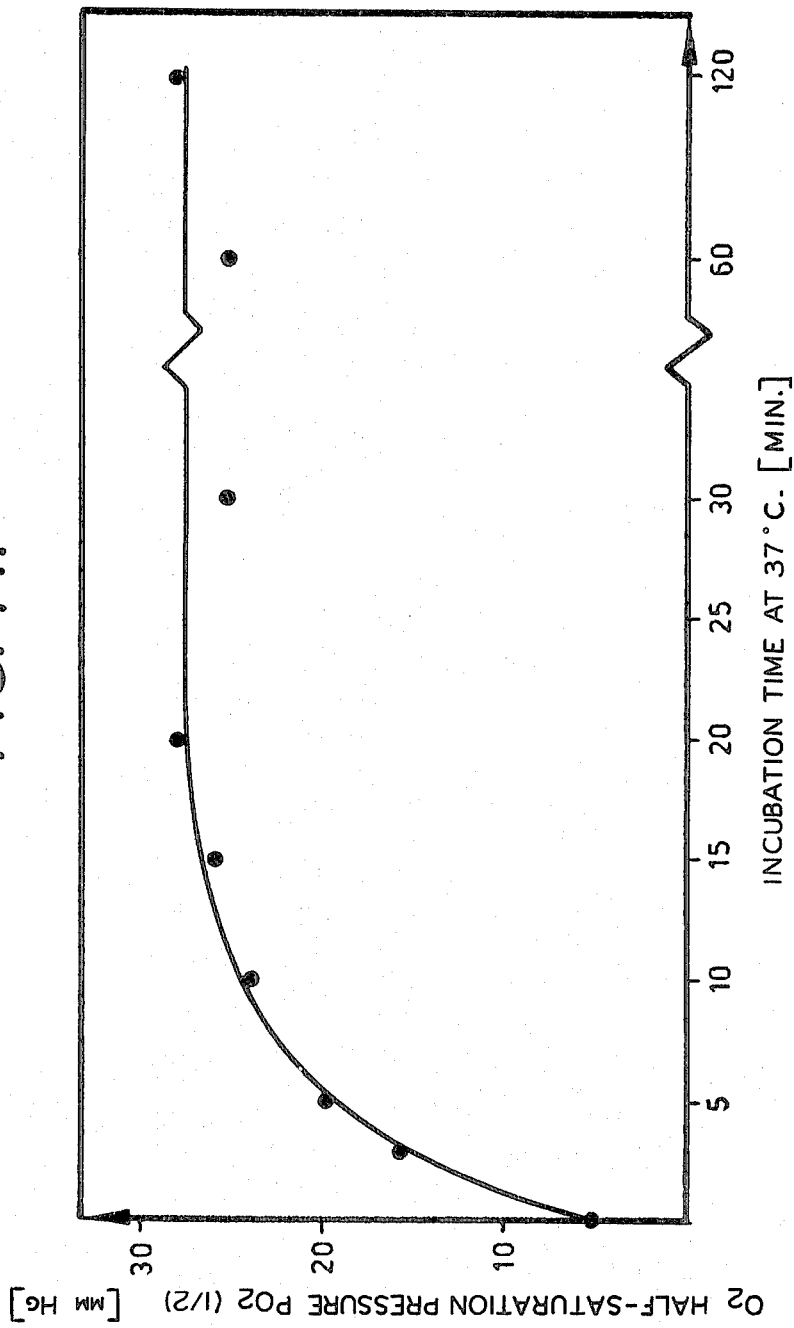
FIG. 14: Kinetics of the V2-mediated IHP incorporation by erythrocytes at pH 7.38 in the presence of IHP in the outer medium. Incubation of 57 days old RBC was carried out under standard conditions. $p_{O_2}(\frac{1}{2})$ was measured at 25° C. in the absence of $CO_2$.

FIG. 14 shows the time-dependent decrease of the O₂ affinity of erythrocytes after incubation with IHP-loaded V2 vesicles in 0.19 M IHP solution at pH 7.35. The increase of $p_{O_2}(\frac{1}{2})$ reaches its half-maximum value after 4 min. The kinetics of IHP incorporation measured as increase of $p_{O_2}(\frac{1}{2})$ depends on the pH of the incubation medium. In FIG. 15 the half-life time of IHP incorporation is plotted versus pH. The uptake of IHP is a slower reaction at low pH (pH 7.3) and a faster reaction at higher pH (pH 7.7). The short half-life time of incorporation at high pH corresponds to the larger amount of IHP incorporated into erythrocytes (c.f. FIGS. 6 and 13).

The kinetics of IHP incorporation is strongly influenced by the presence of free IHP in the outer medium. Removal of free IHP by dialysis or gel filtration of the vesicle suspension leads to an increase of the half-life time of IHP incorporation to 30 min at pH 7.4 (see FIG. 16).

ATP level in IHP-loaded erythrocytes.

The adenosine triphosphate (ATP) content of erythrocytes is of great interest from the viewpoint of red cell preservation and of intact function. The ATP level was measured in red cells having incorporated empty V2 vesicles and IHP-loaded V2 vesicles under the conditions described. All measurements were carried out in isotonic 0.1 M bis-Tris buffer pH 7.4. The ATP concentration was measured with the luciferin-luciferase system:

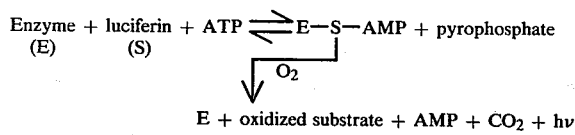

$$E + \text{oxidized substrate} + AMP + CO_2 + h\nu$$

The reaction is so efficient that one proton is produced for each ATP molecule utilized. The incorporation of empty vesicles or of IHP-loaded vesicles is without significant influence on the ATP level in the erythrocytes.

TABLE 2

ATP content of erythrocytes.

$$\left[ \frac{ATP}{\mu M/ml\ RBC} \right]$$

| | |
|---|---|
| Erythrocytes | 0.92 ± 10% |
| Erythrocytes-V2 | 0.84 |
| Erythrocytes-V2-IHP | 0.93 |

The data are for one week-old RBC. The lack of change of the ATP level in the RBC after incorporation of IHP indicates unaltered cell-viability, functionality and plasticity of the RBC.

O₂-releasing effect by fusion of IHP-loaded vesicles with erythrocytes

Figure 17:
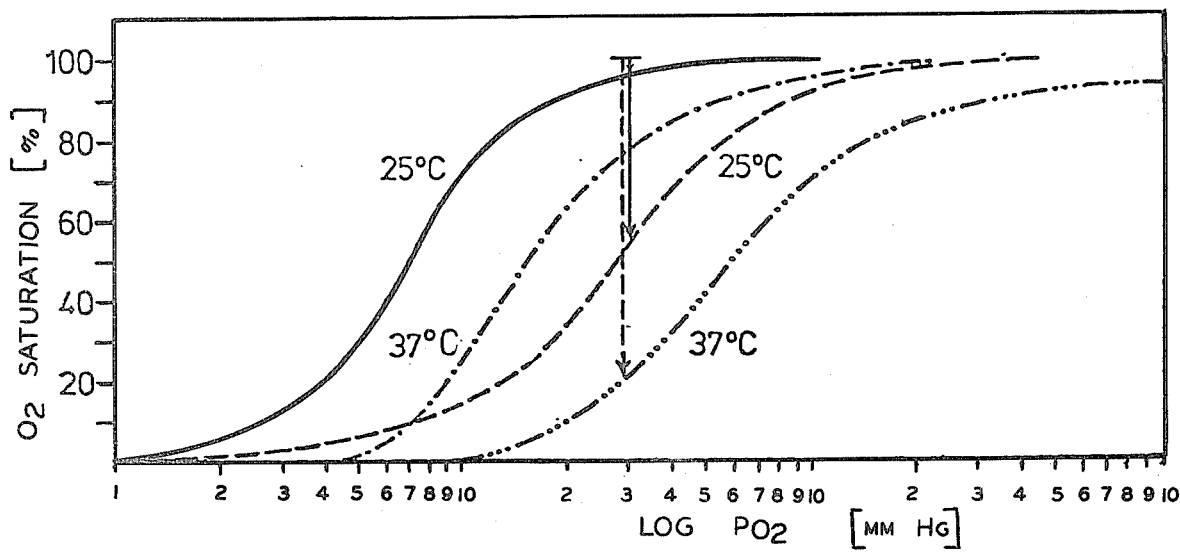
FIG. 17: $O_2$-binding curves before and after V2-mediated IHP incorporation by erythrocytes at pH 7.4. Incubation was carried out under standard conditions at pH 7.6. $O_2$-release by the erythrocytes against the brain critical $O_2$-partial pressure of 30 mm Hg is indicated by arrows: At 25° C.:_____, erythrocytes, 41 days old, (5% $O_2$ release);-------, IHP-loaded erythrocytes (47% $O_2$ release); at 37° C. -.-.-.-, erythrocytes, 41 days old, (21% $O_2$ release); -...-... , IHP-loaded erythrocytes (80% $O_2$ release).

The "right-shift" of the O₂-binding curves after incorporation of IHP is shown in FIG. 17. After fusion of 41-day old erythrocytes, suspended in isotonic bis-Tris buffer, pH=7.4, with the IHP-loaded V2 vesicles the O₂ half-saturation pressure increases from 7 to 28 mm Hg. This means that the normal but aged erythrocytes are loaded at at 25° C. to 95% with O₂ under an O₂-partial pressure of 30 mm Hg, whereas the IHP-loaded erythrocytes contain only 53% of oxygenated haemoglobin under the same conditions. About 60% of the haemoglobin in the erythrocytes has bound IHP after fusion of the IHP-loaded vesicles with the erythrocytes.

Under physiological conditions (at 37° C.) a O₂ half-saturation pressure of 60 mm Hg is computed for the IHP loaded erythrocyates at pH 7.4. Under a critical O₂ partial pressure of 30 mm Hg in the brain, 80% of the haemoglobin from vesicle-treated erythrocytes would release the bound O₂, while normal, untreated erythrocytes would release under these conditions only 20 to 25% of the oxygen. The effective affinity of the erythrocytes can be varied between these two limits either by varying the IHP concentration in the lipid vesicles or the ratio of treated to untreated erythrocytes in blood.

This result shows that the method which we propose in order to incorporate IHP into the erythrocytes provides a lasting, significant and controlled lowering of the O₂ affinity of haemoglobin in intact cells. The erythrocytes thus IHP-loaded are particularly suitable for the control of the O₂ supply of the tissues in the cases mentioned above.

High-altitude adaptation of rats and dogs.

A 200 g rat (body weight) with a blood volume of 14 ml ($p_{O_2}(\frac{1}{2})=14.0$ mm Hg at 25° C. and pH 7.4) was kept in a chamber under decreasing O₂-partial pressure. At an O₂-partial pressure of 120 mm Hg equivalent to an altitude of 13,200 m the rat tumbled down because of O₂ deficiency in the muscles of extremities. Then the O₂ pressure in the chamber was quickly restored to the normal value and the rat behaved normally. From this animal 1 ml blood was collected, the erythrocytes were isolated and loaded with IHP as described in Methods. The IHP-loaded erythrocytes were resuspended in the plasma ($p_{O_2}(\frac{1}{2})=28.0$ mm Hg at 25° C. and pH 7.4) and then retransfused to the rat. After having decreases now the O₂-partial pressure the rat tumbled down at 100 mm Hg ($\triangleq 14,200$ m altitude). This treatment therefore caused in increase of the altitude ceiling of +8%. The altitude adaptation experiment was repeated with this rat 24 h later and lead to the same result.

In another experiment a 9 kg (body weight) dog with a blood volume of 630 ml ($p_{O_2}(\frac{1}{2}) = 10.8$ mm Hg at 25° C. and pH 7.4) was kept in a chamber under decreasing $O_2$-partial pressure. At an $O_2$-partial pressure of 140 mm Hg ($\triangleq 12,200$ m altitude) the dog tumbled down. Then the $O_2$ pressure in the chamber was quickly restored to the normal value and the dog behaved normally. From this dog 100 ml blood were collected, the erythrocytes were isolated and loaded with IHP as described in Methods. The IHP-loaded erythrocytes were resuspended in the serum ($p_{O_2}(\frac{1}{2})=15.0$ mm Hg at 25° C. and pH 7.4) and then retransfused to the dog. After having decreased the $O_2$-partial pressure the dog tumbled down at 110 mm Hg ($\triangleq 13,800$ m altitude). Therefore this treatment caused an increase of the altitude ceiling of +13%. This altitude ceiling was measured over 2 days with the same result.

Both animals were alive and well when last observed, four months (rat) and one month (dog) after the experiments.

Human erythrocytes with high affinity mutant haemoglobin.

A 19 year old female patent with a haemoglobin mutant of unknown structure (Hb$_{Mainz}$) with high $O_2$ affinity donated blood. At 25° C. pH 7.4 her fresh erythrocytes showed a $p_{O_2}(\frac{1}{2})=7.5$ mm Hg. Thus the oxygen supply to the tissues is decreased to 50%. Because of oxygen deficiency in her tissues, this patient receives blood transfusions every six weeks. Loading of these erythrocytes with IHP, as described in Methods, led to an increase of $p_{O_2}(\frac{1}{2})=18.7$ mm Hg. This shows that the high $O_2$ affinity of this patient's blood can be decreased by our method to values being above the normal value of fresh erythrocytes corresponding to an increase of the oxygen supply of +23% of a total blood exchange.

What is claimed is:

1. Lipid vesicles containing inositol hexaphosphate in which the lipid consists essentially of phosphatidylcholine:X:cholesterol in the mole ratio 10 to 5:4 to 1:10 to 3, wherein X is a member selected from the group consisting of stearolyamine, phosphatidic acid, phosphatidyl inositol-phosphate and lysophosphatidyl choline.

2. Lipid vesicles of claim 1 wherein X is stearoylamine.

3. Lipid vesicles of claim 1 wherein X is phosphatidic acid.

4. Lipid vesicles of claim 1 wherein X is phosphatidyl inositol-phosphate.

5. Lipid vesicles of claim 1 wherein X is lysophosphatidyl choline.

6. Lipid vesicles of claim 1 in which the phosphatidylcholine:X and cholesterol are in the mole ratio 8:2:7.

7. Lipid vesicles of claim 1 in which the phosphatidylcholine:X and cholesterol are in the mole ratio 9:1:8.

8. Lipid vesicles of claim 1 in which the phosphatidycholine:X and cholesterol are in the mole ratio 8:4:7.

* * * * *

UNITED STATES PATENT AND TRADEMARK OFFICE
CERTIFICATE OF CORRECTION

PATENT NO. : 4,473,563  Page 1 of 2

DATED : September 25, 1984

INVENTOR(S) : Yves-Claude Nicolau, et al

It is certified that error appears in the above-identified patent and that said Letters Patent is hereby corrected as shown below:

| | |
|---|---|
| Col. 1, line 25 | Delete "efforts" and substitute --effectors-- |
| Col. 3, line 16 | Correct spelling of "Zürich" |
| Col. 4, line 30 | Delete " ✶ " and substitute -- ▫—▫—▫ -- |
| Col. 4, line 31 | Delete symbols after "NaCl" and substitute -- ●—●—● -- |
| Col. 4, line 65 | Delete symbols after "$CO_2$." and substitute -- ●—●—● -- |
| Col. 5, lines 15,16 | Delete symbols after "37°C." and substitute -- ○—○—○ -- |
| Col. 7, line 67 and Col. 8, line 20 | Before "500" delete " $\leqq$ " and substitute -- $\leq$ -- |
| Col. 7, line 68 | Correct spelling of "lipids" |
| Col. 8, line 61 | After "hexaphosphate" delete "." and substitute -- : -- |

UNITED STATES PATENT AND TRADEMARK OFFICE
CERTIFICATE OF CORRECTION

PATENT NO. : 4,473,563                                    Page 2 of 2

DATED : September 25, 1984

INVENTOR(S) : Yves-Claude Nicolau, et al

It is certified that error appears in the above-identified patent and that said Letters Patent is hereby corrected as shown below:

Col. 12, line 36          Correct spelling of "erythrocytes"

Signed and Sealed this

Thirtieth Day of April 1985

[SEAL]

Attest:

DONALD J. QUIGG

*Attesting Officer*          *Acting Commissioner of Patents and Trademarks*